US008461138B2

United States Patent
Boissonneault

(10) Patent No.: US 8,461,138 B2
(45) Date of Patent: Jun. 11, 2013

(54) QUADRAPHASIS CONTINUOUS GRADUATED ESTROGEN CONTRACEPTIVE

(75) Inventor: Roger M. Boissonneault, Long Valley, NJ (US)

(73) Assignee: Warner Chilcott Company, LLC, Farjardo, PR (US)

( * ) Notice: Subject to any disclaimer, the term of this patent is extended or adjusted under 35 U.S.C. 154(b) by 891 days.

(21) Appl. No.: 11/476,675

(22) Filed: Jun. 29, 2006

(65) Prior Publication Data

US 2007/0004690 A1   Jan. 4, 2007

Related U.S. Application Data

(60) Provisional application No. 60/695,093, filed on Jun. 29, 2005.

(51) Int. Cl.
*A61K 31/56* (2006.01)

(52) U.S. Cl.
USPC ........................................................ 514/170

(58) Field of Classification Search
USPC ........................................................ 514/170
See application file for complete search history.

(56) References Cited

U.S. PATENT DOCUMENTS 5,010,070 A * 4/1991 Boissonneault ............... 514/171
RE35,724 E * 2/1998 Pasquale ........................ 514/170

FOREIGN PATENT DOCUMENTS

DE 43 13 926 A1 3/1994
WO WO 2005/049142 2/2005

OTHER PUBLICATIONS

Sep. 13, 2011 Final Office Action issued in connection with U.S. Appl. No. 10/987,653.
Edwards L.A. "An Update on Oral contraceptive Options" Formulary, Advanstar Communications, Cleveland, OH, US, vol. 39, No. 2, Feb. 2004, pp. 104-121.
Hoffman H. et al. "Approaches to the Replacement of Ethinylestradiol by Natural 17β-estradiol in Combined Oral Contraceptives", Jenapharm & Co. KG, Department 9 R&D, Jena, Germany, 1998.

* cited by examiner

*Primary Examiner* — San-Ming Hui
(74) *Attorney, Agent, or Firm* — Fitzpatrick, Cella, Harper & Scinto

(57) ABSTRACT

A quadraphasic estrogenic/progestogenic contraceptive regimen that provides for a low level of estrogen in the initial phase and in the fourth phase is disclosed. Also described is a contraceptive kit that may be used to practice the method of the invention.

10 Claims, No Drawings

QUADRAPHASIS CONTINUOUS GRADUATED ESTROGEN CONTRACEPTIVE

This application claims the benefit of U.S. Provisional Application No. 60/695,093, filed Jun. 29, 2005.

BACKGROUND OF THE INVENTION

1. Field of the Invention

This invention is directed to a method of contraception that provides for the reduced level of estrogen in the initial and final phase of a quadraphasic estrogenic/progestogenic contraceptive regimen without compromising contraceptive efficacy or cycle control. The invention is also directed to a quadraphasic contraceptive kit that may be used to practice the method of the invention.

2. Related Background Art

Contraceptive compositions containing both estrogenic and progestogenic compounds are well known. The progestogenic component of the composition is primarily responsible for the contraceptive efficacy of the composition, while the estrogenic component is employed to reduce undesired side effects, such as breakthrough bleeding or spotting.

The earliest of these estrogenic/progestogenic contraceptive compositions contained a relatively high level of estrogenic component. A constant goal, however, has been to reduce the estrogenic potency of such compositions without reducing contraceptive efficacy and increasing undesired side effects. As described in U.S. Pat. No. 5,888,543, in an attempt to achieve this goal, numerous regimens have been developed in which the progestogen/estrogen combination is administered in a monophasic regimen (fixed dose) or as biphasic or triphasic regimens (varied dose).

A particularly advantageous technique for reducing total estrogenic administration is described in U.S. Pat. No. 4,962,098. This describes a triphasic method of contraception using a progestogen/estrogen combination in which the amount of estrogen is increased stepwise over the three phases. The first phase is 4-7 days, the second phase is 5-8 days and the third phase is 7-12 days. Preferably, the administration of the contraceptive compositions for the three phases will be 21 days followed by a 7 day placebo period. For all three phases the progestogen is 0.5 to 1.5 mg of norethindrone acetate, while about 10 to 30 mcg of ethinyl estradiol is used in the first phase, about 20 to 40 mcg of ethinyl estradiol is used in the second phase and 30 to 50 mcg of ethinyl estradiol is employed in the third phase.

DE 4313926 discloses a 4-phase contraceptive regimen that requires an estrogen and a progestin in the first three seven day phases and an estrogen in the fourth seven day phase. The progestin is only given for 21 days of a 28 day cycle. In addition, when the estrogen is ethinyl estradiol it is suggested that the concentration is stepped down from the phase two composition to the phase three composition in an attempt to mimic a woman's physiological cycle.

There is a continuing desire, however, to further reduce the amount of estrogenic component in an estrogenic/progestogenic composition with continued contraceptive efficacy while avoiding undesired side effects. This invention uses a low level of estrogen in the first phase and replaces the traditional placebo phase with a low level of estrogen to obtain follicular suppression and reduce the potential for endogenous estrogen production.

SUMMARY OF THE INVENTION

This invention is directed to a quadraphasic method of contraception that provides for the reduction of administered ethinyl estradiol without a reduction in contraceptive efficacy or an increase in undesired side effects. This invention essentially replaces the placebo period of a traditional triphasic regimen with a daily dose of ethinyl estradiol. The method of this invention includes administering, in sequential steps, to a female of child bearing age the following compositions: (a) composition I for about 5 to about 9 days; (b) composition II for about 5 to about 9 days; (c) composition III for about 8 to about 12 days; and (d) composition IV for about 2 to about 6 days, and preferably about 4 to 6 days, most preferably about 4 to 5 days. Compositions I, II and III all contain a progestogen in an amount equivalent to about 0.3 to about 1.5 mg, preferably about 0.5 to about 1.5 mg of norethindrone acetate. Composition I contains an estrogen in an amount equivalent to about 2 to about 9 mcg of ethinyl estradiol, both compositions II and III contain an estrogen in an amount equivalent to about 10 to about 50 mcg of ethinyl estradiol and composition IV contains an estrogen in an amount equivalent to about 2 to about 9 mcg of ethinyl estradiol. Composition IV is substantially free of progestogen.

Significantly, the sequential administration of compositions I, II, III and IV is repeated after completion of the administration of composition IV. It is believed that the relatively small amount of estrogen during this progestogen free period will allow for an adequate withdrawal bleed and enhance follicular suppression. It is also preferable that the amount of estrogen be increased by at least an amount equivalent to 5 mcg of ethinyl estradiol between composition II and composition III. In a preferred embodiment of this invention, the estrogen is ethinyl estradiol and the progestogen is norethindrone acetate.

Yet another embodiment of this invention is directed to a quadraphasic combination and contraceptive kit comprising a package containing daily dosages of: (a) a Phase I composition containing a progestogen in an amount equivalent to about 0.3 to about 1.5 mg, preferably about 0.5 to about 1.5 mg of norethindrone acetate and an estrogen in an amount equivalent to about 2 to about 9 mcg of ethinyl estradiol; (b) a Phase II composition containing a progestogen in an amount equivalent to about 0.3 to about 1.5 mg, preferably about 0.5 to about 1.5 mg of norethindrone acetate and an estrogen in an amount equivalent to about 10 to about 50 mcg of ethinyl estradiol; (c) a Phase III composition containing a progestogen in an amount equivalent to about 0.3 to about 1.5 mg, preferably about 0.5 to about 1.5 mg of norethindrone acetate and an estrogen in an amount equivalent to about 10 to about 50 mcg of ethinyl estradiol; wherein the amount of estrogen in the Phase III composition is at least an amount equivalent to 5 mcg of ethinyl estradiol greater than the amount of estrogen in the Phase II composition; and (d) a Phase IV composition containing an estrogen in an amount equivalent to about 2 to 9 mcg of ethinyl estradiol and substantially free of progestogen. Preferably, the estrogen used in the kit is ethinyl estradiol and the progestogen is norethindrone acetate.

DETAILED DESCRIPTION OF THE INVENTION

The method of this invention is practiced by administration of the compositions in a numeric sequence with the Phase I composition being used first, the Phase II composition being used second, etc. If packaging and/or other requirements dictate, the method and kit described herein can be employed as part of a larger scheme for contraception or treatment of gynecological disorders. While the sequence in which Applicant's combinations are administered is important to their operation, it should be kept in mind that variations in timing and dosage can be tolerated when medical considerations so dictate.

Significantly, the method of this invention provides that the sequential administration of compositions I, II, III and IV is repeated after the completion of the administration of composition IV. The daily administration of compositions I, II, II and IV may range from a 20 to a 34 day period. In a particularly preferred embodiment the period of administering compositions I, II and II is 24 days, and period of administering all compositions is 28 days. It is particularly advantageous to administer a progestogen for a 24 day period since this provides consistent suppression of follicular development with an adequate, but shorter withdrawal bleed.

Estrogens which may be used in the present invention include, for example, ethinyl estradiol, 17β-estradiol, 17β-estradiol-3-acetate, mestranol, conjugated estrogens, USP and estrone or salts thereof. The amount of estrogen used is described herein as that which is "equivalent" in estrogenic potency to an amount of ethinyl estradiol. The equivalent estrogenic potency of an estrogen to ethinyl estradiol may be readily determined by one of ordinary skill in the art. It is contemplated that each Phase could employ one or more different estrogens that deliver a potency equivalent to the recited amount of ethinyl estradiol. It is also contemplated that the estrogen used in one Phase may be different than that used in another Phase. In a most preferred embodiment of this invention, however, the estrogen for each Phase is ethinyl estradiol.

Progestogens which may be used in the present invention include, for example, progesterone and its derivatives such as 17-hydroxy progesterone esters and 19-nor-17-hydroxy progesterone esters, 17-alpha-ethinyl testosterone, 17-alpha-ethinyl-19-nortestosterone (norethindrone) and derivatives thereof, norethindrone acetate, norgestrel, nogestamate, desogestrel and D-17-beta-acetoxy-17-beta-ethyl-17-alpha-ethinyl-gon-4-en-3-one oxime. Other exemplary progestogens include demegestone, drospirenone, dydrogesterone, gestodene, medrogestone, medroxy progesterone and esters thereof. The amount of progestogen used is described herein as that which is "equivalent" in progestogenic potency to an amount of norethindrone acetate. The equivalent progestogenic potency of a progestogen to norethindrone acetate may be readily determined by one of ordinary skill in the art. It is contemplated that each Phase could employ one or more different progestogens that deliver a potency equivalent to the recited amount of norethindrone acetate. It is also contemplated that the progestogen used in one Phase may be different than that used in another Phase. In a most preferred embodiment of this invention, however, the progestogen for each of Phase I, II and III is norethindrone acetate and most preferably will be at a constant concentration.

Accordingly, in a preferred embodiment of this invention the compositions employed in accordance with the invention will contain in Phase I about 0.3-1.5 mg, preferably about 0.5-1.5 mg norethindrone acetate and about 2 to about 9 mcg ethinyl estradiol, preferably about 4 to about 6 mcg ethinyl estradiol, in Phase II about 0.3-1.5 mg, preferably about 0.5-1.5 mg norethindrone acetate and about 10-50 mcg ethinyl estradiol, preferably about 20-40 mcg ethinyl estradiol, in Phase III about 0.3-1.5 mg, preferably about 0.5-1.5 mg norethindrone acetate and about 10-50 mcg ethinyl estradiol, preferably about 25-50 mcg ethinyl estradiol, wherein the amount of ethinyl estradiol is increased by at least 5 mcg from Phase II to Phase III, and in Phase IV about 2-9 mcg ethinyl estradiol, preferably about 5 mcg ethinyl estradiol.

A significant aspect of the method and kit of this invention is that the Phase I and IV compositions have a relatively low concentration of estrogen equivalent to ethinyl estradiol, while maintaining contraceptive efficacy and avoiding or minimizing unwanted side effects such as break through bleeding. It is believed that the length of the progestogen regimen of this invention, particularly the preferred embodiment of 24 days of norethindrone acetate, results in an advantageously short withdrawal bleed, e.g., about 3 days. It is further believed that adding estrogen late in the cycle allows for a more developed endometrium and thus a lower incidence of amenorrhea. It is also believed that administration of a low level of estrogen at the end of the quadraphasic regimen will result in improved contraceptive efficacy due to less FSH stimulation. In one particularly preferred embodiment the amount of estrogen equivalent to ethinyl estradiol in the Phase I and Phase IV compositions is about 5 mcg.

The preferred compositions employed in accordance with the invention in Phases I through IV will preferably have the administration times and drug contents set forth in the following table. The table sets forth relevant values for one of Applicant's preferred embodiments, or configurations, for administration of the system to females.

TABLE 1

| Phase | Days | mg Norethindrone acetate | mcg EE |
|-------|------|--------------------------|--------|
| I     | 7    | 1.0                      | 5      |
| II    | 7    | 1.0                      | 25     |
| III   | 10   | 1.0                      | 30     |
| IV    | 4    | —                        | 5      |

The norethindrone acetate (NA) and ethinyl estradiol (EE) are well known and readily available. Clearly, the amount of NA and EE may be varied in accordance with the disclosure of this invention. For example, the amount of NA set forth in Table 1 could readily be adjusted from 1 mg to 0.5 mg or 0.4 mg.

The designation "mcg" refers to micrograms and "mg" to milligrams.

It should be noted that the table is presented for illustrative purposes only. The substitution of functionally equivalent amounts and kinds of reagent(s) in these schemes is contemplated.

The compositions used in this invention are administered using a suitable daily dosage form. Tablets, pills, capsules and caplets are exemplary dosage forms.

In addition, the use of other conventional additives, e.g., fillers, colorants, polymeric binders, and the like is also contemplated. In general any pharmaceutically-acceptable additive which does not interfere with the function of the active components can be used in one or more of the compositions.

Suitable carriers with which the compositions can be administered include lactose, starch, cellulose derivatives and the like used in suitable amounts. Lactose is a preferred carrier. Mixtures of carriers, e.g. lactose, microcrystalline cellulose and starch, are operable.

While the norethindrone acetate is preferred, as previously noted it may be replaced by a different progestogen. Similarly, while the ethinyl estradiol component is preferred it may be completely or partially replaced with one or more conventional estrogenic substances, e.g., mestranol.

The terms "method" and "kit" are used herein to encompass any drug delivery systems via the use of which the 4-phase scheme outlined above can be effectively administered to human females. Combinations of various dosage forms are operable.

A unique dosage pattern, i.e., a unique sequence of administration of a novel estrogen/progestogen combination has been discovered which minimizes the administration of estrogen in the first phase and provides a low level of estrogen administration in the fourth phase of a quadraphasic regimen, while also minimizing certain side effects, notably breakthrough bleeding, commonly associated with conventional low dosage pills. It has also been discovered that the administration of a relatively small amount of estrogen after the third phase allows for an adequate withdrawal bleed and enhances follicular suppression.

Reasonable variations, such as those which would occur to a skilled artisan, can be made herein without departing from the scope of the invention.

What is claimed is:

1. A method of contraception comprising the steps of sequentially administering to a female of child bearing age:
    (a) a composition I containing a progestogen in an amount equivalent to about 0.3 to about 1.5 mg norethindrone acetate and about 2 to about 9 mcg of ethinyl estradiol for about 5 to about 9 days, wherein composition I is the first composition used by the female of child bearing age in the method of contraception;
    (b) a composition II containing a progestogen in an amount equivalent to about 0.3 to about 1.5 mg of norethindrone acetate and about 10 to about 50 mcg of ethinyl estradiol for about 5 to about 9 days;
    (c) a composition III containing a progestogen in an amount equivalent to about 0.3 to about 1.5 mg of norethindrone acetate and about 10 to about 50 mcg of ethinyl estradiol for about 8 to about 12 days; and
    (d) a composition IV substantially free of a progestogen and containing about 2 to about 9 mcg of ethinyl estradiol for about 2 to about 6 days, wherein the amount of ethinyl estradiol in composition III is greater than the amount of ethinyl estradiol in composition II by at least 5 mcg of ethinyl estradiol, the progestogen in composition I, II, and III is norethindrone acetate or norethinedrone and the sequential administration of compositions I, II, III and IV is repeated after the completion of the administration of composition IV.

2. The method according to claim 1, wherein composition I contains an estrogen in an amount equivalent to about 2 to about 5 mcg of ethinyl estradiol.

3. The method according to claim 1, wherein the progestogen in each of compositions I, II and III is norethindrone acetate in an amount from about 0.5 to about 1.5 mg.

4. The method according to claim 1, wherein the progestogen in each of compositions I, II, and III is norethindrone acetate at a constant concentration.

5. The method according to claim 4, wherein composition I contains an amount of ethinyl estradiol from about 2 to about 5 mcg.

6. The method according to claim 5, wherein composition I contains about 5 mcg of ethinyl estradiol.

7. The method according to claim 1, wherein the daily administration of compositions I, II, III and IV is for a 20 to 34 day period.

8. The method according to claim 7, wherein the daily administration of compositions I, II, III and IV is for a 28 day period.

9. The method according to claim 6, wherein composition I contains about 1.0 mg of norethindrone acetate and is administered for about 7 days, composition II contains about 1.0 mg of norethindrone acetate and is administered for about 7 days, composition III contains about 1.0 mg of norethindrone acetate and is administered for about 10 days, and composition IV contains about 5 mcg of ethinyl estradiol and is administered for about 4 days.

10. The method according to claim 9, wherein composition II contains about 25 mcg of ethinyl estradiol and composition III contains about 30 mcg of ethinyl estradiol.

* * * * *

UNITED STATES PATENT AND TRADEMARK OFFICE
CERTIFICATE OF CORRECTION

PATENT NO. : 8,461,138 B2  
APPLICATION NO. : 11/476675  
DATED : June 11, 2013  
INVENTOR(S) : Roger M. Boissonneault Page 1 of 1

It is certified that error appears in the above-identified patent and that said Letters Patent is hereby corrected as shown below:

In the Specification

<u>COLUMN 3:</u>

Line 7, "I, II, II" should read --I, II, III--; and  
Line 10, "I, II, and II" should read --I, II, and III--.

Signed and Sealed this  
First Day of October, 2013

Teresa Stanek Rea  
*Deputy Director of the United States Patent and Trademark Office*